United States Patent [19]
Nguyen et al.

[11] Patent Number: 5,461,925
[45] Date of Patent: Oct. 31, 1995

[54] ASSESSMENT OF DAMAGE IN KERATIN FIBERS

[75] Inventors: Nghi V. Nguyen, Simi Valley; David W. Cannell, Los Angeles; Roger A. Mathews, Newbury Park, all of Calif.

[73] Assignee: Redken Laboratories, Inc., New York, N.Y.

[21] Appl. No.: 218,565

[22] Filed: Mar. 28, 1994

[51] Int. Cl.$^6$ .................................................. G01D 7/02
[52] U.S. Cl. .................. 73/789; 73/160; 73/764; 73/794; 73/828
[58] Field of Search .............................. 73/795, 794, 789, 73/817, 764, 160, 828, 830, 831, 834, 837

[56] References Cited

U.S. PATENT DOCUMENTS

| | | | |
|---|---|---|---|
| 1,932,682 | 10/1933 | Beckley | 73/789 |
| 3,461,718 | 8/1969 | Harvey et al. | 73/789 |
| 3,533,284 | 10/1970 | Slemmons et al. | 73/789 |
| 3,712,124 | 1/1973 | Lutz | 73/789 |
| 3,921,443 | 11/1975 | Yates | 73/789 |
| 4,061,022 | 12/1977 | Yates | 73/789 |
| 4,628,742 | 12/1986 | Golding | 73/829 |
| 4,635,654 | 1/1987 | Mathews et al. | 132/7 |
| 4,665,741 | 5/1987 | Kabacoff et al. | 73/149 |
| 4,862,160 | 8/1989 | Ekchian et al. | 340/825.54 |
| 4,870,391 | 9/1989 | Cooper | 340/572 |
| 4,972,718 | 11/1990 | Said et al. | 73/789 |
| 5,036,308 | 7/1991 | Fockens | 340/572 |
| 5,081,458 | 1/1992 | Meunier | 342/44 |
| 5,103,222 | 4/1992 | Hogen Esch et al. | 340/825.54 |
| 5,105,190 | 4/1992 | Kip et al. | 340/825.54 |
| 5,124,699 | 6/1992 | Tervoert et al. | 340/825.54 |
| 5,218,343 | 6/1993 | Stobbe et al. | 340/572 |
| 5,260,690 | 11/1993 | Mann et al. | 340/572 |

FOREIGN PATENT DOCUMENTS

| | | | |
|---|---|---|---|
| 165035 | 9/1983 | Japan | 73/794 |
| 58-211624 | 12/1983 | Japan | 73/828 |
| 63-273058 | 11/1988 | Japan | 73/828 |
| WO91/14156 | 9/1991 | WIPO | |

OTHER PUBLICATIONS

Edman, et al., "Properties Of Peroxide-Bleached Hair", J. Soc. Cosmet Chem., vol. 12 (#3), 133–145 (1961).
Jachowicz, "Hair Damage And Attempts To Its Repair", J. Soc. Cosmet Chem., 38, 263–286 (Jul./Aug. 1987).
Robbins, "Physical Properties and Cosmetic Behavior Of Hair", *Chemical & Physical Behavior of Human Hair*, Springer-Verlag, 1988, 225–288.
Wolfram, et al., "The Mechanism Of Hair Bleaching", J. Soc. Cosmet Chem., 21, 875–900 (Dec. 9, 1970).

*Primary Examiner*—Richard E. Chilcot, Jr.
*Assistant Examiner*—George M. Dombroske
*Attorney, Agent, or Firm*—Christie, Parker & Hale

[57] ABSTRACT

Keratin fiber condition is evaluated by testing dry hair to determine analysis factors. For each factor, two values of elongation are determined by measuring the force required to obtain a first value and a second value of elongation of the fiber. The percent total elongation of the fiber to its break point is also determined. The ratio of the two measured forces is used with the percent total elongation in empirically derived nonlinear equations to determine analysis factors, such as a condition factor and a moisture factor. It is found that each factor is independent of fiber diameter or the source of the fiber. It is also found that the factors change as a function of subjective or objective measures of chemical damage to, and moisture content of, the hair fiber. The factors can, therefore, be used for identifying hair care products suitable for application to the hair without inducing unacceptable damage. The tests may be performed with simple tensile testing apparatus without tedious examination of the hair under a microscope. Additionally, the hair diameter can be determined by wedging fiber clamps used in the test apparatus.

44 Claims, 9 Drawing Sheets

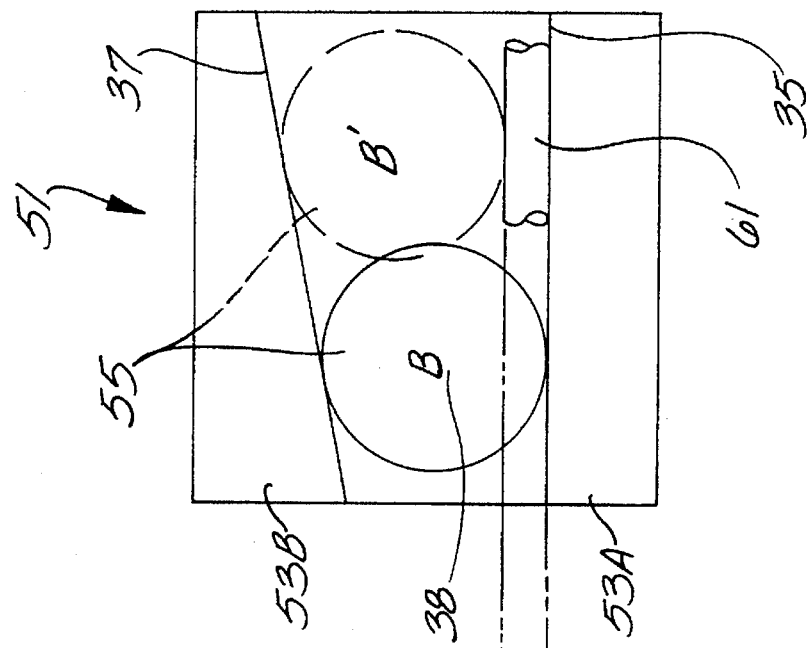
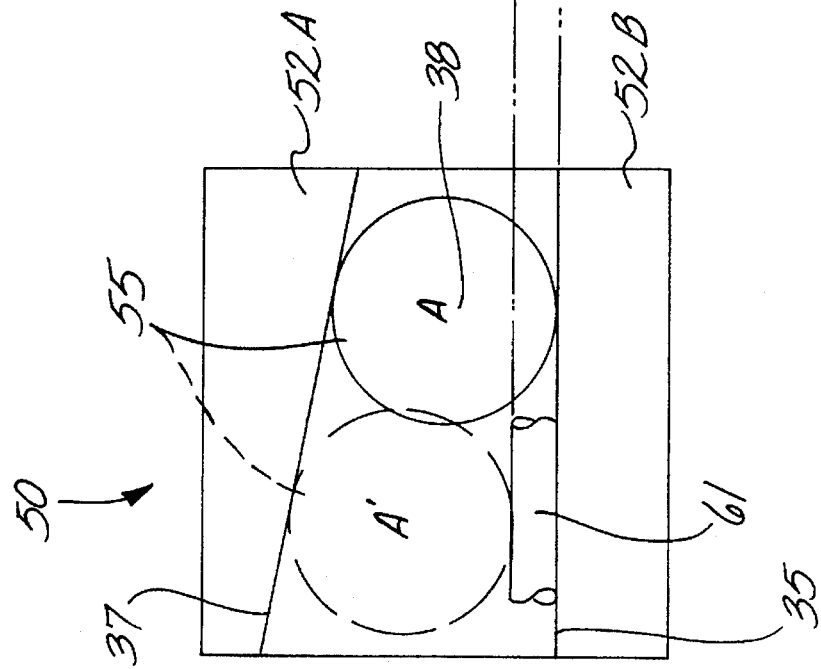
Fig. 6

ASSESSMENT OF DAMAGE IN KERATIN FIBERS

BACKGROUND

An important consideration for a hair stylist preparing to treat a person's hair, is the existing condition of the hair before the treatment commences. For example, the compositions used for applying a permanent wave for a person's hair may be quite different for undamaged hair, which has previously had no more than mild treatment, as compared with hair which has been damaged by repeated bleaching. Highly skilled operators may evaluate the existing condition of the hair and select suitable treatments based on their experience with a variety of subjective visual and tactile examinations.

Such subjective evaluations of the quality of hair and selection of hair care products suitable for application to the hair, are subject to discrepancies due to the experience and skill of the operator. Because of this the optimum hair care products may not be used, and in some cases selection of too harsh a hair care treatment may result in additional damage to hair that is already damaged.

For such reasons, there has long been a desire for objective techniques for evaluating the condition of hair or for determining the level of damage of hair, so that optimum hair care products can be identified. A fairly straightforward idea has been to measure the tensile properties of individual strands of hair. When a keratin fiber such as hair is subjected to tensile force or stress, it is elongated or strained before the force becomes large enough to break the hair. Dry virgin hair, i.e., undamaged hair, may stretch as much as 50% before breaking.

The elongation of a keratin fiber can be represented by a conventional force-elongation curve such as illustrated in FIG. 8 which is typical for dry virgin hair. Stress or force is plotted against strain or percentage elongation. The curve, which has a rather similar shape for all keratin fibers, consists of three regions. The Hookean region, which extends up to about 5% elongation, has a relatively small amount of elongation for a given increment of force, and much of the elongation is elastic. That is, the fiber elongation is generally linear with increasing stress, and upon release of the applied stress, the fiber largely returns to its original length. In the yield region, which extends from about 5% to 30% elongation, there is appreciable elongation for a given increment of applied stress. The post-yield region extends from about 30% elongation to the break point of the fiber. In this region the slope of the force-elongation curve again increases.

The Hookean region represents the force required to overcome coulombic interactions between the side chains of the microfibrillar proteins. The width of the region, and the shape of the curve are affected by moisture content of the fiber, pH and temperature.

The yield region of the force-elongation curve is also sensitive to humidity. The yield region is associated with the transformation of the alpha helical segments of the microfibrillars into beta-sheets.

Beyond 30% elongation the fiber stiffens. In this range, considerably more force must be applied to complete the alpha-beta transformation and to overcome covalent keratin bonds, which are ruptured, leading to breakage of the fiber.

Analysis of the load-elongation or stress-strain curve from a tensile test of fibers, mainly in the yield region, has been the method of choice for assessing damage to keratin fibers. Over the years, several parameters derived from the curve have been employed, with the 20% index being the most commonly used. This index is a ratio of the work required to elongate the fiber by 20% of its original length, after the fiber has been damaged, to the work required to elongate the fiber by 20% before damage. Other investigators have used a 15% index or a 30% index. Any point falling within the yield region may be selected as an index. The advantage of using an index in the yield region, is that the force is relatively constant. Therefore, moderate differences in measurements of fiber elongation do not result in significant variations in the measured force.

A disadvantage of any of these indexes, however, is the force at any point on the force-elongation curve is directly proportional to the diameter of the fiber. For example, oriental hair, generally being coarser, requires more force to stretch it, than does caucasian or negroid hair. Keratin fibers vary greatly in diameter even when taken from a single source. Human hair diameter can vary by as much as 100% on the same head.

Force to elongate a fiber is relatively easy to measure. Stress on the fiber is not easily measured, since it depends on diameter. Researchers have therefore resorted to various, and often tedious, techniques to overcome the diameter related variability of their selected index.

Some investigators test the same fiber before and after treatment. This is accomplished by stretching the fiber in water before treatment to the desired elongation, and then allowing that fiber to relax back to near the original condition. The assumption has been that the stretching does not affect the tensile properties of the fiber significantly. The relaxation process usually requires 24 hours, after which the fiber is treated (e.g., permed, bleached, straightened or dyed) and then retested. Despite the reliability of the technique, the time consuming relaxation process makes the technique inefficient and rather unappealing.

Another technique employed to overcome diameter effects is to test fibers of comparative diameter. This necessitates the aid of a microscope to scan fibers for homogeneity along the tested length and to sort the fibers according to size. This technique can be stressful to the investigator, inefficient when large numbers of samples are to be analyzed, and require additional costly equipment. Thus, even in a laboratory setting there is a great need for a simple fast technique, utilizing the properties of the force-elongation curve independently of fiber diameter and humidity.

The stress-strain curve techniques mentioned may be suitable for a laboratory environment where "before and after" testing is conducted. This is not of direct assistance to a salon operator who wishes to evaluate preexisting hair conditions before adopting a course of treatment. A "before and after" type evaluation is inapplicable. Even so, some measure of hair quality may be obtained by such an index, since the stress required for a given elongation of the hair tends to be reduced by damage to the internal structure of the hair. Salon operators may use a tensile testing machine and microscope to measure hair diameter and strength for evaluating a client's hair condition. Not only is such equipment costly, the time required for reliable testing is a precious commodity and few operators perform such objective testing.

Yet another technique employed to overcome diameter effects is to test fibers by measuring the force required to elongate the fiber by a first percentage of its length, measuring the force required to elongate the fiber by a second percentage of its length, and determining the ratio between these two forces. As described in U.S. Pat. No. 4,972,718, incorporated by reference herein, this ratio represents a constant intrinsic property of virgin keratin fibers independent of fiber diameter, and independent of the source of the fiber. As the force ratio increasingly deviates from the force ratio for virgin fibers, it indicates increasing damage to the internal protein structure of the fiber.

However, this ratio method preferably requires that the hair has been wetted sufficiently to substantially neutralize interactions other than breaking cystine bonds in order to determine the ratio of forces required for obtaining the given two values of elongation. Additionally, this ratio method generally lacks the ability to determine other characteristics of the fiber, e.g., such as moisture content.

Thus, there remains a desire for a simple and fast technique, in the context of a salon, for evaluating hair damage without wetting the hair first, and for determining moisture content. This technique is desired so that the hair stylist may, before treatment commences, select the desired hair care product for a given client. Preferably, the technique is independent of other properties of the hair such as diameter, which is a tedious measurement. It is therefore desirable to provide a novel method and apparatus for analyzing hair condition, moisture, texture, and diameter.

There are other keratin fibers where a fast, simple and reliable test for condition of the fibers is useful. For example, buyers and users of wool presently evaluate quality by subjective visual and tactile factors. It is desirable to provide objective measures of wool quality which can be used by skilled or relatively unskilled persons with reliability.

BRIEF SUMMARY OF THE INVENTION

There is, therefore, provided in practice of this invention according to a presently preferred embodiment, a method and apparatus of hair analysis comprising determination of fiber condition, moisture content and diameter by physical means alone. This invention also relates to a hair clamping mechanism that is a design feature of the apparatus by which the fiber diameter is measured.

In a preferred embodiment of this invention, there is a method for evaluating the condition of a keratin fiber by determining at least one analysis factor for the keratin fiber. The analysis factor is determined by empirically derived mathematical equations. The equations are nonlinear relationships between an analysis factor and measured coefficients. Coefficients of the equations are determined preferably by measuring the force required to elongate the fiber by a first percentage of its length, measuring the force required to elongate the fiber by a second percentage of its length, determining the ratio between these two forces, and determining the percentage of fiber elongation from no elongation to a break point of the fiber.

More specifically, the present invention relates to an improved method and apparatus for the analysis of hair without requiring that it first be wetted. This new method analyzes force and elongation data. The data are derived by extending a dry human hair at ambient relative humidity (R.H.) and a controlled rate of elongation, for example, about 1 inch (2.5 cm) per minute, until the fiber breaks. The force and elongation data so derived can be used to calculate a condition factor, $F_c$. This factor $F_c$ correlates to the condition of the hair protein structure, as judged by direct chemical analysis of cysteic acid and intact cystine in the hair sample. The force and elongation data can also be used to calculate a moisture factor, $F_m$, that correlates to the total moisture content of the hair. Both the "condition factor," $F_c$, and the "moisture factor," $F_m$, are relatively independent of the diameter of the fiber.

One such analysis factor comprises a condition factor $F_c$ which is equal to Logarithm (base 10) $E_B \times (F_2/F_1)^2$, where $E_B$ is a measured elongation to a break point of the fiber, $F_1$ is a measured force at a first elongation point, $F_2$ is a measured force at a second elongation point. The other analysis factor comprises a moisture factor $F_m = E_B \times$ Logarithm $(F_4/F_3)$, where $E_B$ is a measured elongation to a break point of the fiber, $F_3$ is a measured force at a first elongation point and $F_4$ is a measured force at a second elongation point.

It has been discovered that these analysis factors represent a constant intrinsic property of virgin keratin fibers independent of fiber diameter, and surprisingly, independent of the source of the fiber. Further, it is found that as an analysis factor value increasingly deviates from a known analysis factor value for virgin fibers, it indicates, for example, the relative moisture content of the fiber, or increasing damage to the internal protein structure of the fiber.

There is also provided, in practice of this invention according to a presently preferred embodiment, a novel method for determining the diameter of a keratin fiber. The diameter is determined by using a clamping arrangement which also holds the keratin fiber during measurement of the analysis factor coefficients. The apparatus disclosed herein enables precise measurement of fiber diameter. This precision is approximately in the range of $\pm 1 \times 10^{-6}$ meters, hereinafter microns (mµ). This measurement of fiber diameter is useful to the professional cosmetologist in adjudging the "texture" of the hair. The texture of hair can be defined, for example, as "fine" being less than 60 mµ; "medium" being approximately 60–90 mµ; and "coarse" being greater than 90 mµ.

The technique may be performed with an apparatus which applies an elongating force to a keratin fiber and has means for determining the forces required to obtain each of the selected values of elongation of the fiber. Means can be provided for displaying an analysis factor or for storing a plurality of analysis factors obtained by testing several fibers and displaying an average of a number of analysis factors. Such apparatus may include means for identifying a hair care product suitable for application to the tested hair, as a function of an analysis factor.

BRIEF DESCRIPTION OF THE DRAWINGS

These and other features and advantages of the present invention will be appreciated as the same becomes better understood by reference to the following detailed description when considered in connection with the accompanying drawings wherein.

Figure 7:
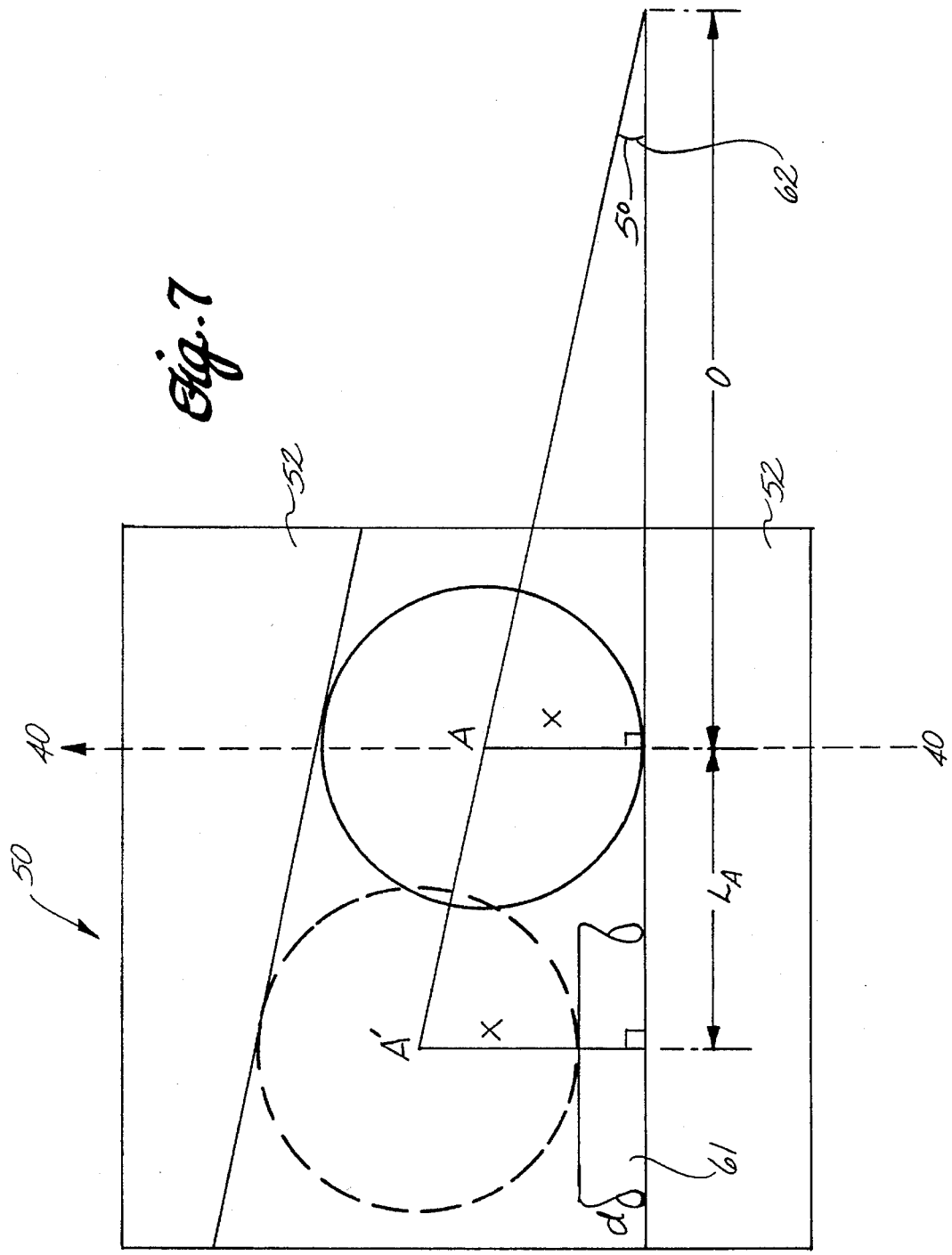
Figure 8:
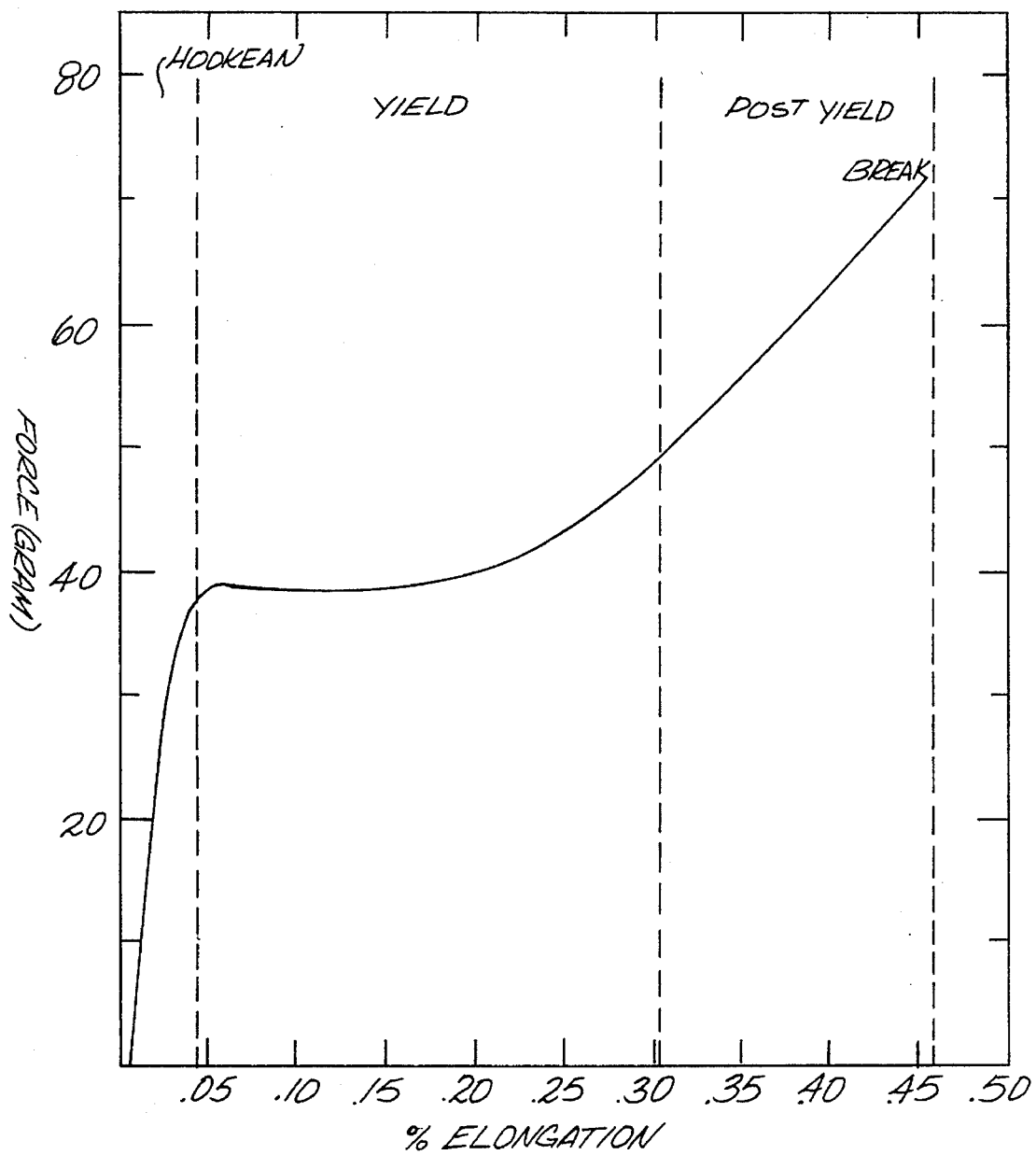

F.;

FIG. 6 is a schematic diagram of the clamping mechanism as described in this invention;

FIG. 7 is a schematic diagram of the clamping mechanism that is used to measure the diameter of the keratin fiber;

FIG. 8 is a typical force-elongation curve for dry virgin hair; and

Figure 9:
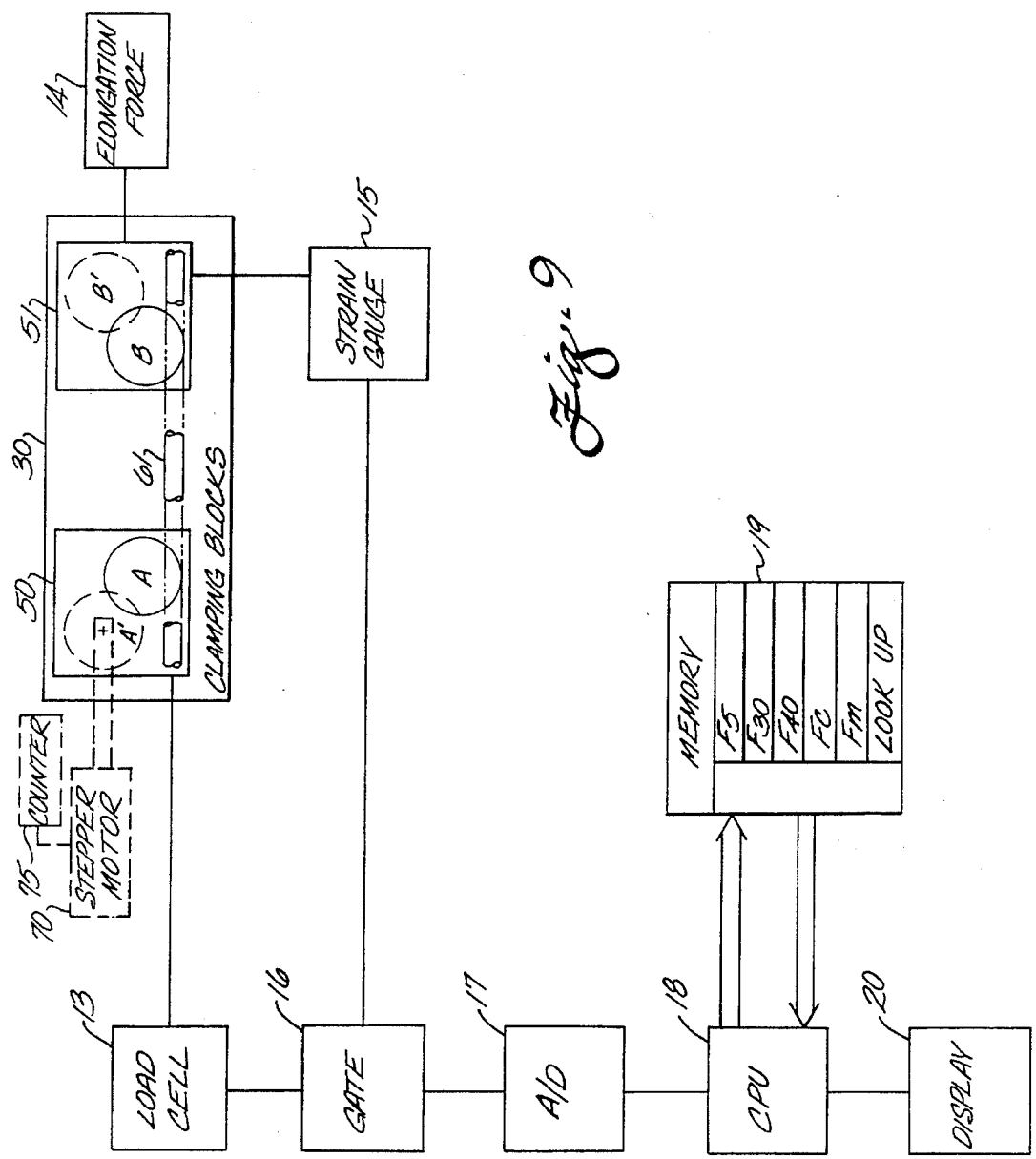

FIG. 9 illustrates in block form an apparatus for evaluating keratin fiber condition using the novel analysis factors.

DETAILED DESCRIPTION

It has been discovered that certain analysis factors, mathematically derived from the relationship of measured coefficients occurring substantially in the post-Hookean region of the force-elongation curve, are substantially constant. The analysis factors remain substantially constant, regardless of fiber diameter or source, for an untreated keratin fiber that is stretched under appropriate conditions. The keratin fiber, or hair, is preferably not wetted. Load should be applied to the fiber at a constant rate of elongation to eliminate a possible variable.

The derived analysis factors therefore represent a constant intrinsic property of virgin keratin fibers. The factors also represent dimensionless parameters, such as a condition factor and a moisture factor. These factors have been found to be diagnostic of the internal structural integrity of the fiber, and of the moisture content of the fiber, respectively. Damage to the cystine bonds of the hair results in a measurable change in the condition factor which can be correlated with the subjective condition diagnosis of a person's hair. Also, moisture content of the hair results in a measurable change in the moisture factor which can be correlated with the subjective moisture diagnosis of a person's hair.

To obtain measured coefficients, a typical procedure is to position a strand of hair between the grips of a tensile testing apparatus with a selected gauge length, one inch (25 mm), for example. Suitable tensile testers are described and illustrated in U.S. Pat. Nos. 3,921,443 to Yates, 4,061,022 to Yates, and 4,628,742 to Golding, incorporated by reference herein. Alternatively, an Instron tensile tester Model No. 1122 equipped with a 500 gram tension load cell and data recorder may be used. A variety of other tensile testing devices on the market may also be used.

The hair is stretched at a constant rate, for example one inch (25 mm) per minute, through all regions of the force-elongation curve. The force required to obtain a given elongation is recorded for each elongation value desired. For purposes of determining a condition factor $F_c$, determining the force required to obtain 5% elongation and the force required to obtain 30% elongation are convenient. For purposes of determining a moisture factor $F_m$, determining the force required to obtain 30% elongation and the force required to obtain 40% elongation are convenient. For both factors, the total elongation to fiber break point is also recorded. There is no need for tedious examination of the hair under a microscope because the technique is independent of hair diameter, as shown below.

Although forces recorded at any elongation value can be used, it is preferable to record forces corresponding to elongations occurring within the yield and post-yield regions of the force-elongation curve. In the preferred arrangement, the force $F_5$ at 5% strain and the force $F_{30}$ at 30% strain have been found to be desirable for the condition factor. Also, in the preferred arrangement, the force $F_{30}$ at 30% strain and the force $F_{40}$ at 40% strain have been found to be desirable for the moisture factor.

Preferably, when the forces at two points on the force-elongation curve have been determined for a given analysis factor, a force ratio, which can be generically designated $F_B/F_A$, is calculated. Next, the analysis factor is calculated according to the appropriate equation described below. Both a force ratio, and the value of total elongation expressed in percent, are used to calculate the analysis factor. Preferably, the test is repeated with from five to ten different fibers, with the analysis factor calculated for each fiber. The average of the separate analysis factors are calculated to provide a reported analysis factor. Either the analysis factor or a correlative objective or subjective characterization can be reported to the operator. Alternately, any or all of these values can be displayed if desired.

More specifically, in the preferred arrangement, the present invention comprises the tensile analysis of a human hair fiber and subsequent calculation of a "Condition Factor," $F_c$, and a "Moisture Factor," $F_m$, according to the following equations:

$$F_c = \text{Logarithm } E_B \times (F_{30}/F_5)^2$$

$$F_m = E_B \times \text{Logarithm } (F_{40}/F_{30})$$

Where:

(1) $E_B$ is percent elongation to a break point of the fiber.

(2) $F_5$ is the force in grams at 5% elongation.

(3) $F_{30}$ is the force in grams at 30% elongation.

(4) $F_{40}$ is the force in grams at 40% elongation.

(5) "Logarithm" is the logarithm base 10.

The force $F_{30}$ is preferably used twice, occurring once in each of the equations that determine $F_c$ and $F_m$. This dual use of $F_{30}$ has been found to be sufficient for determining the hair analysis factors, based upon empirical results. Also, this dual use of $F_{30}$ eliminates the need to make a fourth force measurement. However, it is within the scope of this invention that $F_{30}$ could be replaced with unique and different measurements for the $F_c$ and $F_m$ equations, such that four measurements would be required.

The present invention further comprises the determination of fiber diameter by an apparatus which preferably performs such analyses in tandem with the tensile testing. Both the $F_c$ and $F_m$ relationships were derived empirically by using both computer-assisted curve fitting of relative humidity, and cysteic acid data versus force/elongation data.

Figure 1:
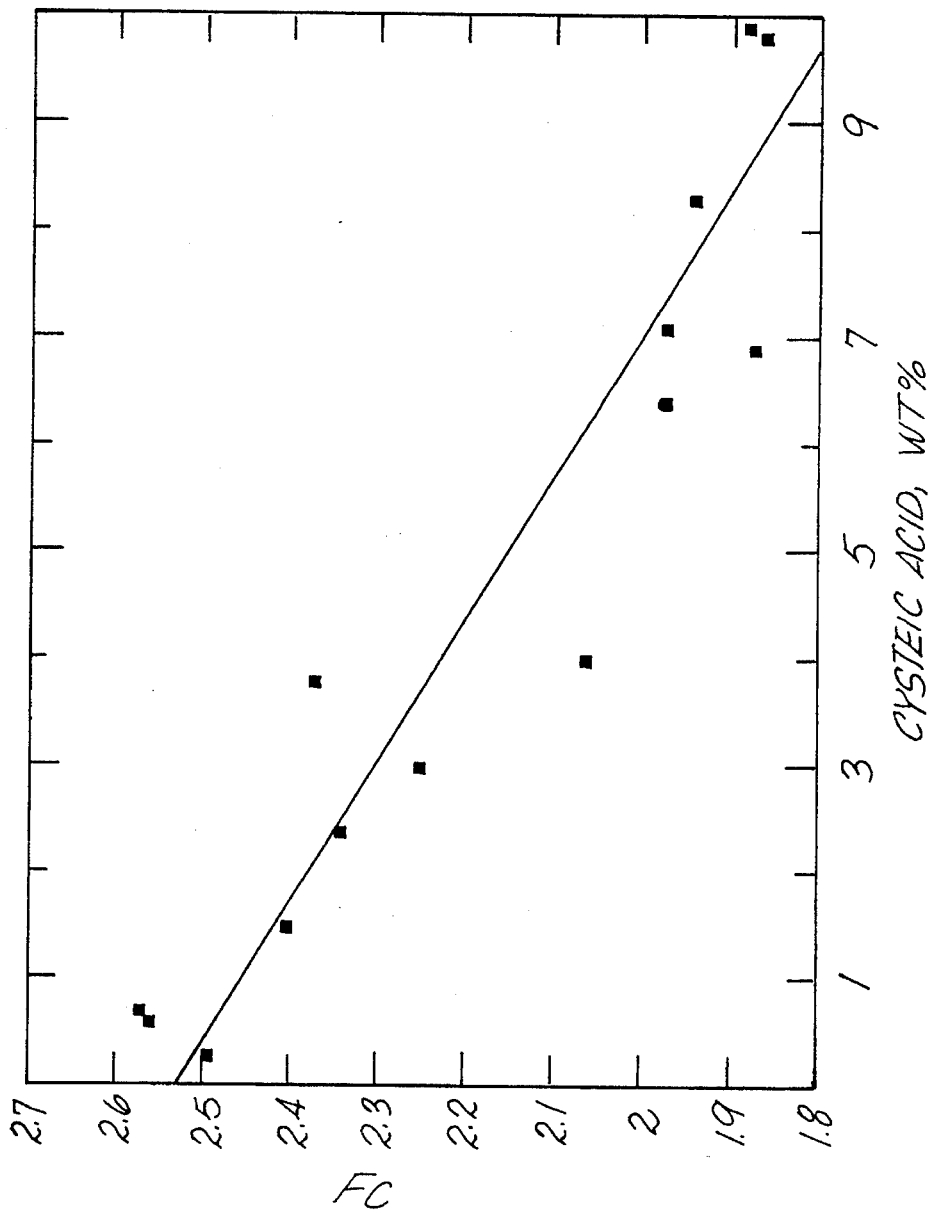
FIG. 1 is a typical curve comparing $F_c$ versus the content of cysteic acid at 40% relative humidity.

The relationship between the condition factor, $F_c$, and hair condition, i.e., cysteic acid, at 40% relative humidity is shown in FIG. 1. As the damage to hair increases, as judged by the chemical treatments applied to the hair and its resulting content of cysteic acid, the $F_c$ decreases in an approximately linear fashion.

The condition factor actually diagnoses the internal condition of the keratin protein. A typical virgin keratin fiber has about 16% cysteine molecules involved in disulfide bonds. Chemical treatment of the hair may irreversibly break some of the sulfur bonds, yielding two derivatives of cysteine molecules. A principal portion of the strength of the hair is damaged as the cystine bonds are broken. Perming the hair involves temporary breaking of the cystine bonds, styling the hair, and restoring most of the cystine bonds. Excessive perming with strong solutions or too long an exposure to the solution, or repeated bleaching can irreversibly damage the cystine bonding.

Figure 2:
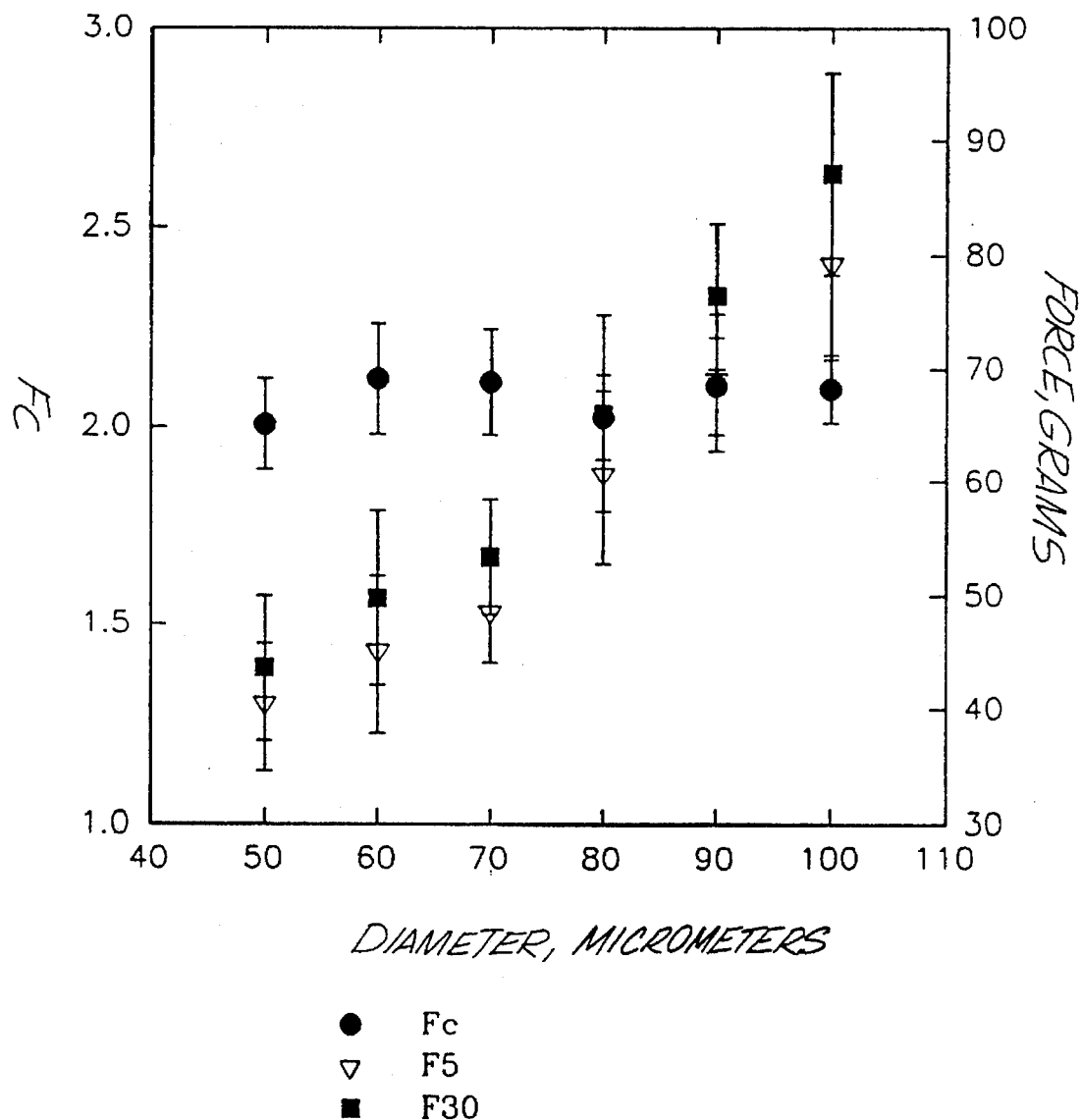
FIG. 2 is a graph illustrating the diameter independence of $F_c$ in bleached hair which has been tested at 45% relative humidity and 72° F.

The diameter-independence of $F_c$ is demonstrated in FIG. 2. As expected, the measured forces required for 5% and 30% elongation of the fiber are dependent on fiber diameter. But surprisingly, $F_c$ shows little such diameter dependence.

In testing various types of hair, the data obtained indicates a strong correlation of approximately 90% between $F_c$ and fiber damage. This correlation occurs both in laboratory damaged tresses and in salon client sourced hair. Therefore, $F_c$ is a reasonably reliable measure of hair condition.

Figure 3:
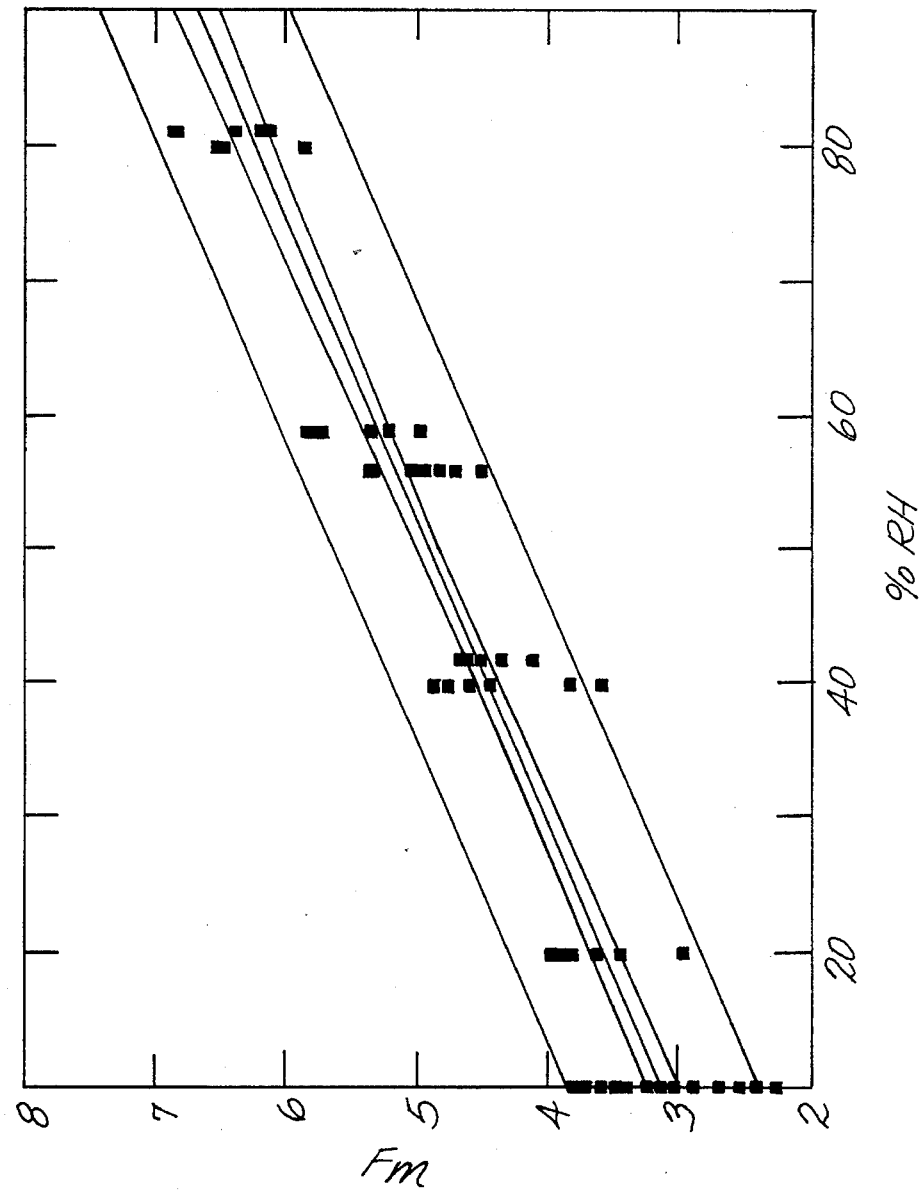
FIG. 3 is a typical chart illustrating the relationship between $F_m$ and the percent relative humidity present.

The relationship between the moisture factor, $F_m$, and relative humidity is shown in FIG. 3 for various hair conditions. FIG. 3 shows an approximately 90% linear correlation between $F_m$ and relative humidity. $F_m$ can be used to determine the ambient relative humidity of the fiber environment by reading a chart such as the one shown in FIG. 3.

Figure 4:
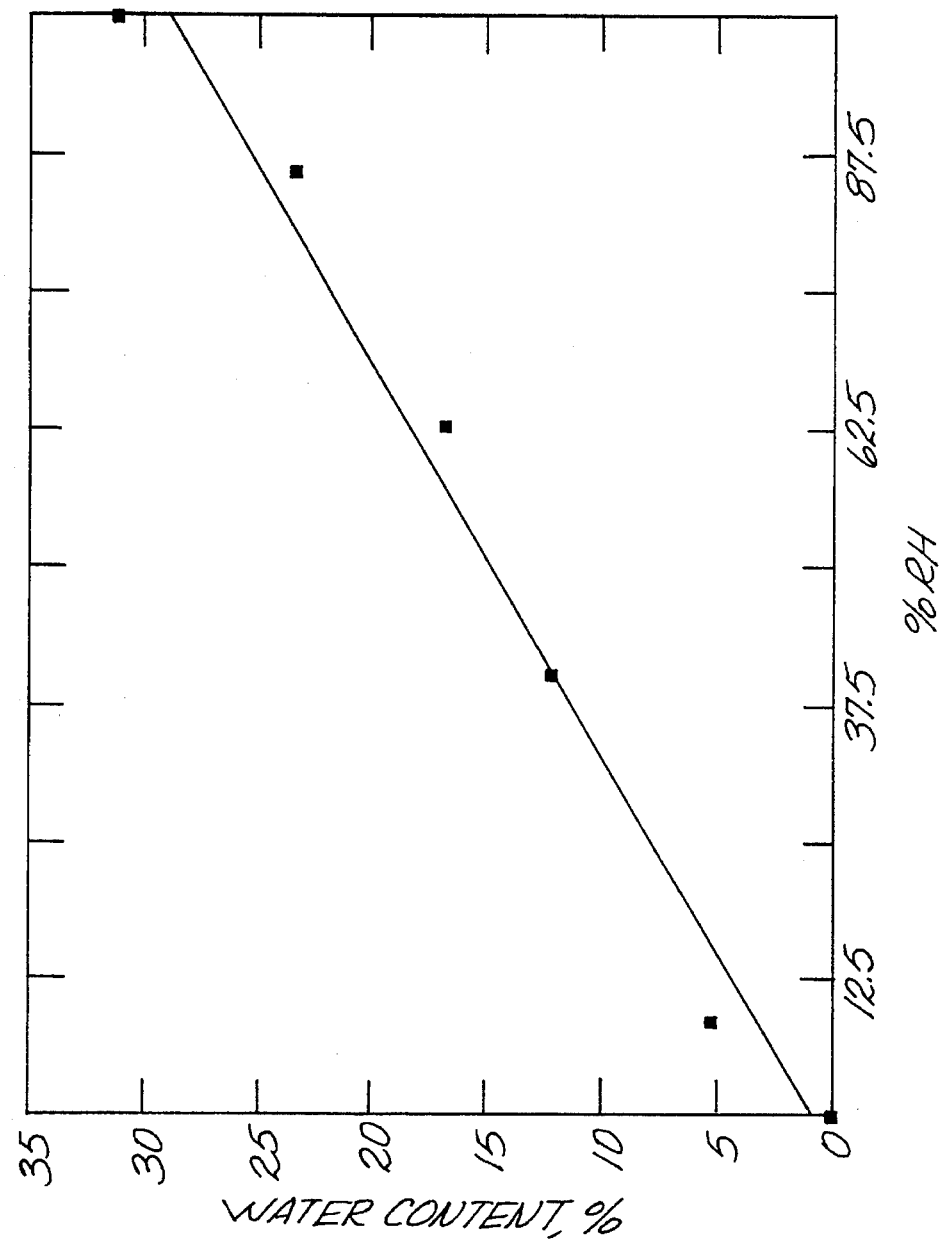
FIG. 4 is a typical chart illustrating the water content determination in percent as compared to the percent relative humidity.

The substantially linear relationship between the relative humidity associated with the fiber environment and the actual water content of the hair fiber is shown in FIG. 4. The actual water content of the hair fiber can be deduced from the fiber's relative humidity value by reading a chart such as the one shown in FIG. 4. In a preferred embodiment, $F_m$ is correlated with water content to classify the fiber into preferably three subjective moisture content categories. The moisture content of the fiber is an indication of the state of the protein in the hair which can be objectively and subjectively graded.

Figure 5:
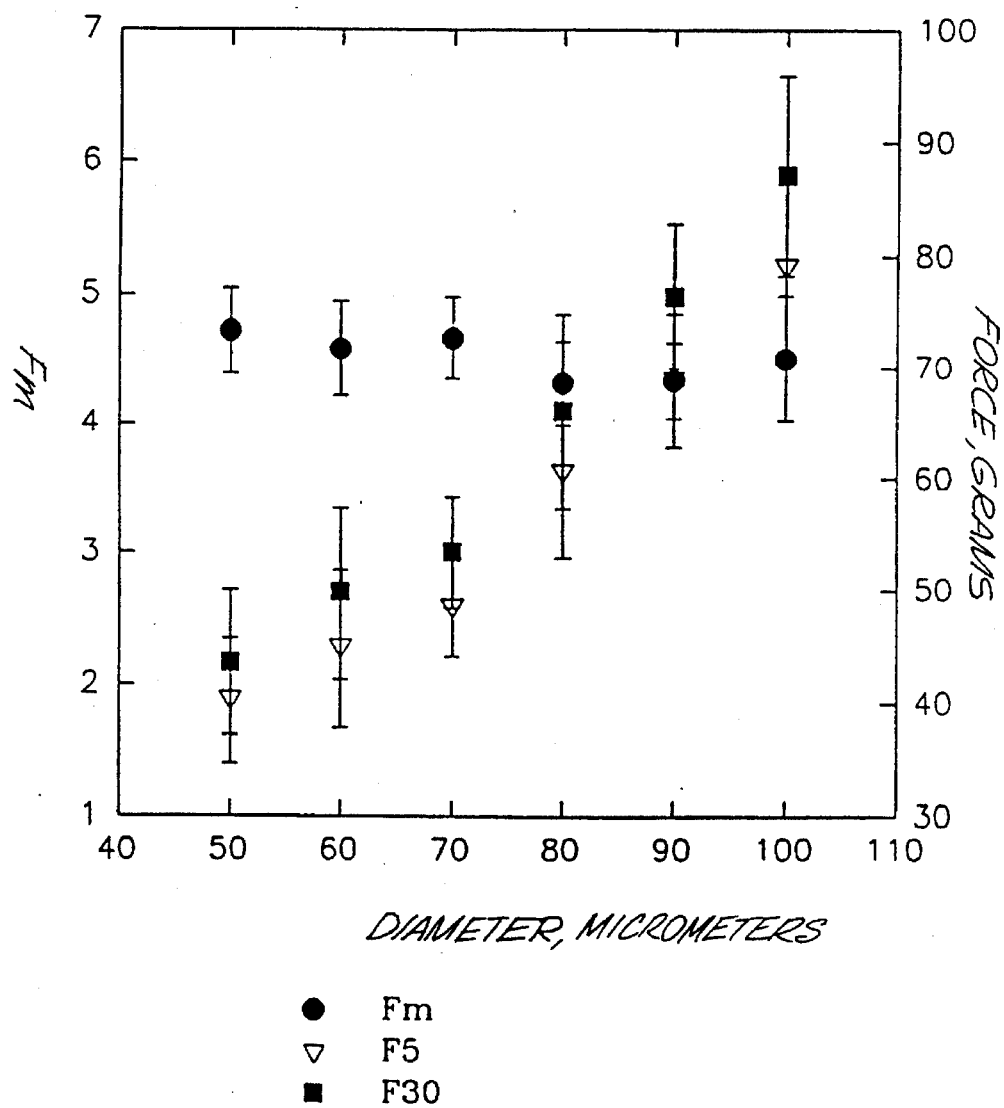
FIG. 5 is a graph illustrating the diameter independence of $F_m$ in bleached hair tested at 45% relative humidity and 72°

The diameter-independence of $F_m$ is demonstrated in FIG. 5. Again, as expected, the measured forces required for 5% and 30% elongation of the fiber are dependent on fiber diameter. But surprisingly, $F_m$ also shows little such diameter dependence.

The previously mentioned tensile testing apparatus may also be used in conjunction with the following modifications as desired. The modifications permit the user to determine the fiber diameter as well as provide for fiber clamping as shown in FIGS. 6 and 7 in schematic form.

The measurement of hair diameter is a direct consequence of the hair clamping, lead screw and stepper motor mechanisms of the preferred arrangement. The hair clamps serve two functions: 1) to clamp hair for tensile testing, and 2) to work in conjunction with other parts of the machine as a measuring device.

FIG. 6 shows a clamping arrangement of the invention. Under normal conditions, a first clamp 50, and a second clamp 51, are used to hold a keratin fiber 61 for testing. Each clamp operates to hold a keratin fiber in substantially the same manner. Each clamp holds an opposing end of the same fiber, for applying stress to the fiber by elongating it. Each clamp is constructed of a lower block piece 52B, 53B and an upper block piece 52A, 53A. The lower block piece cooperates with the upper block piece to form two converging wedging surfaces. The converging wedging surfaces are comprised of a lower wedging surface plane 35 and an upper wedging surface plane 37, respectively. Each clamp is arranged so that a fiber end is located between the two surface planes. The upper and lower surfaces converge toward the center of the fiber. This results in the two surfaces being arranged such that the wedging surface planes are farther apart, i.e., wider, nearer the fiber end, and closer together, i.e., narrower, toward the fiber's center, such that each set of surfaces creates a wedging space between them.

For each clamp, a cylinder 55 is placed between the upper and lower surface planes, with the cylinder's axis of rotation 38 parallel to both surface planes. The cylinder is placed between the surfaces such that it clamps the fiber end region between it and the lower surface. The cylinder is wedged between the upper inclined surface plane and the fiber, which in turn is wedged against the flat lower surface plane.

As the clamps are moved apart to elongate a fiber, the fiber end is urged from the wider end to the narrower end of each clamp. As the fiber end moves toward the narrow end of the clamp, the cylinder is cooperatively urged toward the narrow end as well. This causes the cylinder to cam against the fiber end and hold it in place.

As shown in FIGS. 6 and 7, when a keratin fiber is introduced into the clamping mechanism, both cylinders 55 are pushed back to a new position A' and B' respectively. In other words, a displacement "d", the diameter of the hair 61, has moved each cylinder back a distance "$L_A$". When a tensile test is started, the second clamp 55 is moving away from the first clamp 50. At this point, the two cylinders in the two clamps are pulled toward each other. In effect, they "wedge" the hair in place as shown in FIGS. 6 and 7.

The preferred procedure for measuring hair diameter, i.e., the "d" displacement is as follows. First, the separation of the clamp is measured from the first and second clamp positions A, B to the respective clamp positions A', B'. This separation is measured by a counter 75 that counts the steps displaced by the stepping motor 70 (FIG. 9). Each step of the motor is equal to 6 mμ. For example, displacement "$L_A$" is equal to the number of motor steps used to move the cylinder 55 from the position A to a new location of A'. The taper angle 62 is fixed at 5°, and cooperates to form part of a triangle with side "O" as shown in FIG. 7. By analyzing the relationship as shown in FIG. 7, it is understood from trigonometric analysis that:

$$\tan(5°) = x/o = (x+d)/(L_A+O)$$

From this analysis, it can be mathematically derived that the hair diameter "d" is equal to the result of counting the number of steps to move a distance $L_A$ and dividing by 11.4.

In other words, there is a mechanical advantage of 11.4:1 by obtaining the value d in this manner, as opposed to stepping the motor up and down perpendicular to the hair diameter, such as along line 40 in FIG. 7, at 6 micron increments. If the diameter were determined by merely counting the motor steps along line 40, then the measurement would not be nearly as precise. With the converging surfaces engaging the cylinder of fiber, diameter measurements are made with approximately 0.5 micron precision. Additionally, parameters such as radius and cross-sectional area can be determined with the same apparatus and appropriate means for calculation.

The clamps 55 are displaced a distance $L_A$ when a keratin fiber is placed in the clamps. The precision of measuring the diameter can be improved by averaging the reading from each clamp. To obtain the value "d" using a plurality of clamps, the equipment software handles the calculation based on the same or a substantially similar mathematical analysis as previously described.

In the practice of this invention, it is preferable to use the trigonometric relationship of tangent. However, in alternate embodiments, other trigonometric relationships can be used as desired. For example, a cotangent trigonometric relationship may be used to define an equation for the determination of "d".

Also, the shape of the clamps and of the cylinder can be altered, such that shapes other than a wedge or a cylinder are used, as desired. For example, rather than the cylinder's substantially tangent point contact of the fiber, a flat contact member can be used. A flat member is more likely to sense the true maximum diameter, as it will contact a greater length portion of fiber than the cylinder. However, the wedge and cylinder embodiment is sufficient for the preferred practice of this invention.

In a preferred practice of the invention, the cosmetologist samples the client's hair by collecting samples from various locations on the head. The cosmetologist also gives special attention to, and selects from, the more damaged areas of hair. For example, surface hair, hair from around the hairline and/or damaged hair ends are selected. The hair samples are then loaded and sequentially tested in the hair analysis unit. The unit measures the hair diameter and then proceeds to the tensile testing. During tensile testing the hair is extended to its break point ($\%E_B$). While extending the hair, force data at 5%, 30% and 40% elongation are collected and stored in machine memory. The data is then used to calculate the $F_c$ and $F_m$ factors. These factors relate directly to the protein condition and the moisture content of the hair.

$F_c$ values are subjectively graded for the type of hair as follows:

| $F_c$ Value | Hair Condition Diagnosis | Approx. % of Cysteic Acid (wt %) |
|---|---|---|
| Caucasian/African | | |
| >2.85 | Competent | <1% |
| 2.55 to 2.85 | Weakened | 1 to 3% |
| 2.25 to 2.54 | Fragile | 3 to 5% |
| <2.25 | Degraded | >5% |
| Oriental | | |
| >2.90 | Competent | <1% |
| 2.55 to 2.90 | Weakened | 1 to 3% |
| 2.25 to 2.54 | Fragile | 3 to 5% |
| <2.25 | Degraded | >5% |

$F_m$ values are subjectively graded as follows:

| $F_m$ Value | Hair Moisture Content Diagnosis | Approx. Moisture Content (wt %) |
|---|---|---|
| >5.5 | Excessive Moisture | >15% |
| 4.8–5.5 | Normal Moisture | 12 to 15% |
| <4.8 | Diminished Moisture (Dry) | <12% |

There is generally a correlation between the water content of the hair fiber and the ambient relative humidity that the fiber is most recently been exposed to. $F_m$'s value is affected by the ambient relative humidity. In other words, $F_m$ values vary depending upon the relative humidity that the fiber has been recently exposed to. Therefore, a person living in a relatively humid climate, such as Houston, would have an $F_m$ value and a hair moisture content that would be higher than the same person's hair after spending some time in a relatively dry climate, such as Phoenix.

While the $F_m$ determination is not independent of the ambient relative humidity, determination of $F_m$ is still of value. It has been found that by using only, for example, three broad categories of moisture content, the use of $F_m$ is a sufficiently accurate guide for selecting hair care products. The three categories presently used are excessive moisture, normal moisture and diminished (dry) moisture content. A person's hair that is exposed to varying relative humidities will exhibit respectively varied $F_m$ data points as well. However, these data points, for example, may will fall within a range of 3%, such as 12–15% water content for the fiber, depending on the ambient relative humidity. By using broad categories, such as 12–15% water content equal to normal hair, excessively moist hair having a water content above about 15% and dry hair having moisture content of less than 12%, the problems from variations induced by different ambient relative humidity are significantly less. Use of the broad categories allows for the $F_m$ value, i.e., the moisture content of the hair value, to be used to select a line of hair care products for dry, normal or excessively moist hair.

The purpose of this $F_m$ determination is a guide to the selection of hair care products. The $F_m$ value is not meant to be an analytical tool for precise determination of water content of fibers. $F_m$ can only be used as a precise analytical tool when a relatively precise measurement of the ambient relative humidity that the fiber is known to be exposed to, is also taken and factored into the calculation. Nevertheless, it has been discovered that grouping the hair into broad categories of moisture content is "close enough" to provide an improved ability to recommend a set of hair care products based upon the $F_m$ analysis factor.

An important utility of the analysis factors is their diagnostic capability. Accurate assessment of the integrity of the keratin proteins of hair is vital for reducing the risk of chemically overprocessing the hair and causing damage. This is particularly important in the salon environment where the previous history of treatment of the hair may not be known, and unfortunate results may be avoided.

The machine will, based on the above, report a subjective "Condition" and "Moisture" diagnosis and grade the hair diameter into a subjective "texture" category as follows:

| Diameter Range | Texture Diagnosis |
|---|---|
| <60 microns | Fine |
| 60–90 microns | Medium |
| >90 microns | Coarse |

The diagnostic data from the client's hair test is then used by the instrument to: (a) prescribe the appropriate at-home product regimen, for example, shampoo, rinse, conditioner treatment, (b) prescribe the appropriate in-salon treatment, and (c) indicate if the client's hair can tolerate a permanent waving procedure and, if so, the permanent wave products most appropriate for the client's hair. The client diagnosis and product recommendation can then be sent to an external printer and/or computer for storage and/or retrieval.

It is also found that the analysis factors are substantially independent of the source of the keratin fiber. They are not only substantially independent of the ethnic background for human hair, but also for the limited testing done, are independent of the species. It has been found that the analysis factors are substantially the same for oriental black hair, negroid hair, blond caucasian hair and albino hair, as well as non-human hair.

To measure the coefficients needed for the above equations, one may simply use a chart recorder or X-Y plotter for plotting a force-elongation curve. One can then manually measure the forces at selected elongations and calculate the analysis factors. It is preferable, however, to provide automatic equipment which can be easily operated by an inexperienced hairstylist in a salon environment. Such equipment may also be used for automatically identifying exemplary hair care products suitable for treatment of hair as a function of the analysis factors.

FIG. 9 illustrates in block diagram form suitable apparatus for obtaining the desired factors and hair diameter. Exemplary tensile testing apparatus may be similar to that described in the aforementioned U.S patents. Such apparatus comprises a fiber clamping block and cylinder arrangement 30 as previously described, in which a strand of hair 61 is continually elongated to the break point of the fiber. The substantially fixed first clamp 50 is connected to a conventional load cell 13 for measuring the tensile load on the strand of hair. Means 14 are provided for applying an elongation force for moving the second clamp 51 away from the first clamp 50 and thereby elongating the strand of hair. The elongation force may be applied at a constant rate by a screw, cam, or hydraulic actuator.

The second clamp 51 is also connected to a strain measuring gauge 15 for determining the elongation of the strand of hair. A gate 16 permits reading of the load cell for measuring the force applied to the hair when the strain gauge records a selected elongation, such as 5%, 30%, and 40%. These forces $F_5$, $F_{30}$, and $F_{40}$ are converted to digital values by an analog to digital converter 17 and fed to a digital central processing unit 18. The forces $F_5$, $F_{30}$, and $F_{40}$ are temporarily stored in a memory 19. The CPU also calculates analysis factors as set forth by the aforementioned equations for each fiber tested, and the resultant analysis factors are also stored in the memory.

As shown in FIG. 9, the first clamp 50 is suitably connected to a force transducer or load cell 13. The second clamp 51 is connected to a means for applying an elongation force 14. The means for applying an elongation force may be a screw drive, hydraulic cylinder or other means for gradually moving the second clamp away from the first clamp.

Preferably, when a number of fibers have been tested, the operator causes the CPU to calculate an average of the stored analysis factors for the fibers and the average is shown on a display 20. The operator may also select a certain desired treatment, such as a permanent wave, and key that treatment into the CPU. The apparatus then searches a look-up table in the memory for identifying a permanent wave lotion, or the like, suitable for application to hair with the measured analysis factors. The identified product or products are also displayed or may be provided in the form of a personalized printout of hair care products suitable for the hair of the individual tested.

As has been shown, the analysis factors indicate cysteic acid content and a moisture content of the hair, respectively. Thus, if desired the display can back correlate to cysteic acid content and display a cysteic acid index which is a function of $F_c$. Similarly, if desired the display may show a moisture index which is a function of $F_m$. These indexes may be indicated numerically or by a qualitative characterization such as "dry", "normal" or "moist".

Although described in one embodiment, it will be apparent that the invention may be practiced otherwise than specifically described. In the examples given it is assumed that testing is in a salon environment for evaluating the condition of a customer's hair before treatment. It will also be apparent that such a technique is of considerable value for research and for evaluation of existing or proposed hair treatment compositions or regimen, to determine the extent of damage of the disulfide hair bonds that occurs by reason of such treatment. It will also be apparent that this invention is also suitable for testing the quality of wool or other keratin fibers which are presently largely judged on a subjective basis.

The preferred elongation force measurement points for each analysis factor may be varied as desired for a particular purpose. Thus, different elongation force measurement points may be appropriate for testing wool or for evaluating experimental compositions to obtain a different sensitivity than appropriate for determining hair damage in a salon environment.

While only preferred arrangements of the invention are described herein in detail, the invention is not limited thereby. It is believed that the advantages and improved results of the invention will be apparent from the foregoing description. It will be apparent that various changes and modifications may be made without departing from the spirit and scope of the invention as sought to be defined in the following claims.

What is claimed is:

1. A method for analyzing keratin fiber comprising the steps of:

measuring a first force required to obtain a first value of elongation of a keratin fiber, wherein the first force is less than the force required to reach the break point elongation region of the force-elongation curve;

measuring a second force required to obtain a second, relatively higher, value of elongation of a keratin fiber wherein the second force is less than the force required to reach the break point elongation region of the force-elongation curve;

determining a force ratio of the second force and the first force;

determining a representation of fiber elongation that occurs as measured from substantially no elongation to a break point of the fiber; and determining at least one analysis factor that is directly proportional to a nonlinear mathematical function of the force ratio and the representation of fiber elongation.

2. A method as recited in claim 1 comprising the substantially concurrent step of determining the diameter of the keratin fiber while measuring the forces.

3. A method as recited in claim 1 comprising the step of determining a logarithmic nonlinear function.

4. A method as recited in claim 1 wherein the nonlinear function is exponential.

5. A method as recited in claim 1 wherein an analysis factor is a condition factor $F_c = \text{Logarithm } E_B \times (F_2/F_1)^2$;

wherein $E_B$ is a measured elongation to a break point of the fiber;

wherein $F_1$ is a measured force of a first elongation;

wherein $F_2$ is a measured force of a second elongation; and wherein the Logarithm is a logarithm base 10.

6. A method as recited in claim 1 wherein an analysis factor is a moisture factor $F_m = E_B \times \text{Logarithm } (F_4/F_3)$;

wherein $E_B$ is a measured elongation to a break point of the fiber;

wherein $F_3$ is a measured force of a first elongation;

wherein $F_4$ is a measured force of a second elongation; and wherein the Logarithm is a logarithm base 10.

7. A method as recited in claim 1 wherein the analysis factor is a measure of moisture content of a keratin fiber.

8. A method as recited in claim 1 wherein the analysis factor is a measure of cysteic acid content of a keratin fiber.

9. A method as recited in claim 1 comprising the step of selecting a hair care product as a function of at least one such analysis factor.

10. A method for analyzing keratin fiber comprising the steps of:

measuring a first force required to obtain a first value of elongation of a keratin fiber, wherein the first force is less than the force required to reach the break point elongation region of the force-elongation curve;

measuring a second force required to obtain a second, relatively higher, value of elongation of a keratin fiber wherein the second force is less than the force required to reach the break point elongation region of the force-elongation curve;

determining a force ratio of the second force and the first force;

determining a representation of fiber elongation that occurs as measured from substantially no elongation to a break point of the fiber; and determining at least one analysis factor that is a measure of moisture content of a keratin fiber that is directly proportional to the mathematical product of the representation of fiber elongation and the logarithm of the force ratio.

11. A method for analyzing keratin fiber comprising the steps of:

measuring a first force required to obtain a first value of elongation of a keratin fiber, wherein the first force is less than the force required to reach the break point elongation region of the force-elongation curve;

measuring a second force required to obtain a second, relatively higher, value of elongation of a keratin fiber wherein the second force is less than the force required to reach the break point elongation region of the force-elongation curve;

determining a force ratio of the second force and the first force;

determining a representation of fiber elongation that occurs as measured from substantially no elongation to a break point of the fiber; and determining at least one analysis factor that is a measure of cysteic acid content of a keratin fiber that is directly proportional to the mathematical product of the logarithm of the representation of fiber elongation and the square of the force ratio.

12. A method for evaluating the condition of hair comprising the steps of:

measuring the force required to elongate a strand of hair a first percentage of its length;

measuring the force required to elongate the strand of hair a second percentage of its length;

determining a force ratio between the first and second forces;

determining a measure of fiber elongation that occurs as measured from substantially no elongation to a break point of the fiber; and determining at least one analysis factor that is proportional to the force ratio and the measure of fiber elongation at the break point of the fiber, wherein the proportionality is to the logarithm of the measure of fiber elongation to the break point of the fiber.

13. A method as recited in claim 12 wherein the first and second percentages each lie within the range defined by the yield and post-yield regions of a force-elongation curve of the strand.

14. A method as recited in claim 12 comprising the step of selecting a hair care product as a function of at least one such analysis factor.

15. A method for evaluating the condition of hair comprising the steps of:

measuring the force required to elongate a strand of hair a first percentage of its length;

measuring the force required to elongate the strand of hair a second percentage of its length;

determining a force ratio between the first and second forces;

determining a measure of fiber elongation that occurs as measured from substantially no elongation to a break point of the fiber; and determining at least one analysis factor that is proportional to the force ratio and the measure of fiber elongation at the break point of the fiber, wherein the proportionality is to the logarithm of the force ratio.

16. A method as recited in claim 15 wherein the first and second percentages each lie within the range defined by the yield and post-yield regions of a force-elongation curve of the strand.

17. A method as recited in claim 15 comprising the step of selecting a hair care product as a function of at least one such analysis factor.

18. A method for evaluating the condition of hair comprising the steps of:

measuring the force required to elongate a strand of hair a first percentage of its length;

measuring the force required to elongate the strand of hair a second percentage of its length;

determining a force ratio between the first and second forces;

determining a measure of fiber elongation that occurs as measured from substantially no elongation to a break point of the fiber; and determining at least one analysis factor that is proportional to the force ratio and the measure of fiber elongation at the break point of the fiber, wherein the proportionality is to the square of the force ratio.

19. A method for evaluating the condition of hair comprising the steps of:

measuring the force required to elongate a strand of hair a first percentage of its length;

measuring the force required to elongate the strand of hair a second percentage of its length;

determining a force ratio between the first and second forces;

determining a measure of fiber elongation that occurs as measured from substantially no elongation to a break point of the fiber;

determining at least one analysis factor that is proportional to the force ratio and the measure of fiber elongation at the break point of the fiber; and determining the moisture content of a keratin fiber as a function of the determined analysis factor.

20. A method as recited in claim 19 wherein the first and second percentages each lie within the range defined by the yield and post-yield regions of a force-elongation curve of the strand.

21. A method as recited in claim 19 comprising the step of selecting a hair care product as a function of at least one such analysis factor.

22. Apparatus for assessing condition of a keratin fiber comprising:

means for applying an elongating force to a keratin fiber;

means connected to the means for applying force, for determining a ratio of forces required to obtain each of two selected values of elongation of the keratin fiber within the range defined by the yield and post-yield regions of the force-elongation curve for the fiber;

means connected to the means for applying force, for determining fiber elongation that occurs as measured from substantially no elongation to a break point of the fiber;

means for determining the fiber diameter by determining a distance from a means for clamping without a fiber present to the means for clamping with a fiber present, wherein the means for clamping is moved along a line that converges relative to a length of the fiber;

means connected to the means for determining a ratio and to the means for determining a quantity of fiber elongation, for determining at least one analysis factor as a function of both the force ratio and the quantity of elongation; and means connected to the means for determining at least one analysis factor, for displaying at least one analysis factor.

23. Apparatus as recited in claim 22 wherein the means for displaying comprises means for displaying a cysteic acid index which is a function of at least one analysis factor.

24. Apparatus as recited in claim 22 wherein the means for displaying comprises means for displaying a moisture index which is a function of at least one analysis factor.

25. Apparatus as recited in claim 22 further comprising means for selecting a hair care product as a function of at least one such analysis factor.

26. Apparatus for evaluating condition of hair comprising:

means for elongating a hair fiber;

means connected to the means for elongating, for measuring force applied to the fiber at each of first and second selected elongations;

means connected to the means for measuring, for determining the ratio of the first and second forces;

means connected to the means for elongating, for determining an assessment of fiber elongation that occurs as measured from substantially no elongation to a break point of the fiber;

means connected to the means for determining a ratio and to the means for determining an assessment of fiber elongation, for determining at least one analysis factor that is proportionally related to a nonlinear equation of the force ratio and the assessment of fiber elongation; and means connected to the means for determining at least one analysis factor, for displaying at least one analysis factor.

27. Apparatus as recited in claim 26 wherein the means for determining a nonlinear mathematical function comprises means for determining an exponential function of the force ratio.

28. Apparatus as recited in claim 26 wherein the means for determining a nonlinear mathematical function comprises means for determining a logarithm function of the force ratio.

29. Apparatus as recited in claim 26 wherein the means for determining a nonlinear mathematical function comprises means for determining a logarithm function of the assessment of fiber elongation.

30. Apparatus as recited in claim 26 wherein the means for displaying comprises means for displaying a moisture index which is a function of at least one analysis factor.

31. Apparatus as recited in claim 26 wherein the means for displaying comprises means for displaying a cysteic acid index which is a function of at least one analysis factor.

32. Apparatus as recited in claim 26 further comprising means for selecting a hair care product as a function of at least one such analysis factor.

33. A method for analysis of keratin fibers comprising:

determining a fiber "condition factor," designated $F_c$, according to the following equation:

$$F_c = \text{Logarithm } E_B \times (F_2/F_1)^2;$$

wherein $E_B$ is a measured elongation to a break point of the fiber;

wherein $F_1$ is a measured force of a first elongation;

wherein $F_2$ is a measured force of a second elongation;

wherein the Logarithm is a logarithm base 10; and determining the cysteic acid content of a keratin fiber as a function of the determined condition factor.

34. A method for analysis of keratin fibers comprising:

determining a fiber "moisture factor," designated $F_m$, according to the following equation:

$$F_m = E_B \times \text{Logarithm } (F_4/F_3);$$

wherein $E_B$ is a measured elongation to a break point of the fiber;

wherein $F_3$ is a measured force of a first elongation;

wherein $F_4$ is a measured force of a second elongation;

wherein the Logarithm is a logarithm base 10; and determining the moisture content of a keratin fiber as a function of the determined moisture factor.

35. A method as recited in claim 34 comprising the step of selecting a hair care product as a function of at least one such moisture factor.

36. A method as recited in claim 34 comprising the step of selecting a hair care product as a function of at least one such moisture factor and at least one factor related to hair condition.

37. Apparatus for clamping and determining the diameter of a hair fiber comprising:

a fixed surface for receiving a hair fiber;

a member movable along a path parallel to the length of a fiber on the fixed surface and converging toward the fixed surface for clamping the fiber;

means for measuring travel of the movable member in a direction along the length of the fiber; and means for determining the thickness of the fiber as a trigonometric function of travel of the movable member.

38. Apparatus as recited in claim 37 wherein the means for measuring travel comprises:

means for measuring travel of the movable member parallel to the fiber, and further comprising means for multiplying the distance traveled by the tangent of the angle of convergence.

39. Apparatus as recited in claim 37 wherein the movable member comprises a cylindrical surface.

40. Apparatus as recited in claim 37 comprising a stepping motor for moving the movable member and the means for measuring travel comprises means for counting the number of steps between a first position where the member is in contact with the fixed surface and a second position where the member is in contact with a hair fiber clamped between the member and the fixed surface.

41. A method for measuring hair diameter comprising the steps of:

placing a hair fiber on a flat surface;

moving a member along a path converging toward the flat surface until the member engages the hair fiber and clamps the hair fiber between the member and the flat surface;

determining the distance between the locus of the member when engaged with the hair fiber and the locus of the member when engaged with the flat surface; and multiplying the distance by a trigonometric function of the angle of convergence.

42. A method comprising performing the clamping, determining, and multiplying steps as recited in claim 41 on a second portion of the hair fiber and averaging the diameters determined.

43. A method as recited in claim 41 further comprising the steps of:

wedging a part of the fiber between the member and the flat surface with sufficient pressure to immobilize the fiber such that a portion of the fiber can be elongated to a break point of the fiber.

44. A method as recited in claim 41 comprising counting the number of steps of a stepping motor between a first position where the member is in contact with the fixed surface and a second position where the member is in contact with a hair fiber clamped between the member and the fixed surface.

* * * * *